United States Patent [19]

Bushman

[11] Patent Number: 5,264,916
[45] Date of Patent: Nov. 23, 1993

[54] OBJECT DETECTION SYSTEM

[75] Inventor: Boyd B. Bushman, Lewisville, Tex.

[73] Assignee: Lockheed Corporation, Ft. Worth, Tex.

[21] Appl. No.: 851,281

[22] Filed: Feb. 7, 1992

[51] Int. Cl.$^5$ .............................. G01J 4/00; G01J 1/01
[52] U.S. Cl. ..................................... 356/364; 359/371; 359/407; 359/501; 250/330; 250/342
[58] Field of Search ............... 356/364, 366, 367, 368; 359/371, 386, 407, 483, 485, 501; 250/330, 342

[56] References Cited

U.S. PATENT DOCUMENTS 3,549,259  12/1967  Klatchko .
4,202,601   5/1980  Burbo et al. .................. 350/159
4,601,552   7/1986  Jessmore ...................... 350/551
5,138,162   8/1992  Hacskaylo .................... 250/330

*Primary Examiner*—Mark Hellner
*Attorney, Agent, or Firm*—James E. Bradley; Charles E. Schurman

[57] ABSTRACT

A device will detect man-made objects by using a polarizer. The polarizer rotates about an axis in front of a lens array. The rotation of the polarizer alternately polarizes light received in proportion to the speed of rotation. This produces flashing in intensity for detecting the object as well as background rejection due to its lack of polarization. A man-made object having both horizontal and vertical surfaces of a type that will reflect light that can be polarized will provide flashing through the lens array as the polarizer passes through horizontal and vertical position. On the other hand, backgrounds don't have polarized components and won't flash. Attention is drawn to the man-made target. The background can also be electronically eliminated from the observed scene, permitting precise lock-on to the target.

56 Claims, 5 Drawing Sheets

OBJECT DETECTION SYSTEM

BACKGROUND OF INVENTION

1. Field of Invention

This invention r in general to detecting objects by detecting light reflections from an object, and in particular to a system that utilizes a polarizer for viewing the differences between vertical and horizontal polarization of the light reflected from an object.

2. Description of the Prior Art

This invention deals with a method of detecting objects, such as military targets. The targets may be trucks, tanks, artillery, aircraft, command centers and other systems. These objects may be protected by camouflage, foliage, or may be painted with a camouflage paint.

Presently, objects are detected visually through binoculars. Objects also may be detected by other techniques such as radar, infrared and night vision amplification systems. The prior systems do not always adequately detect an object, particularly objects that are camouflaged.

There are needs for detecting objects other than in military applications also. For example, the highest reason for helicopter crashes is due to collisions with hightension electric wires, guy wires or other suspended cables. These cables are difficult to see by the pilot. At present, there is no particular means for detecting such cables other than visually.

SUMMARY OF THE INVENTION

In this invention, a light ray polarizer is employed for detecting objects. The polarizer is of a conventional type, having a large number of very finely spaced parallel lines or a polarizing filter. Military vehicles have high concentrations of non-conductors of electricity, such as glass, plastic, paints, rubbers, etc. Non-conductors have a high light contrast or modulation when seen by a polarizer that is rotated. The polarizer observes this polarized light effect only when it is sequentially oriented in certain rotational positions. The polarized reflected light from these objects is extremely different in intensity from light reflected from these objects that is not polarized. Consequently, rotating a light polarizer in front of a lens system will cause a man-made object such as a military vehicle, appear to flash as the polarizer rotates between the polarizing positions. The contrast is even more pronounced on overcast days.

Natural backgrounds do not show the polarizing contrast because of their textures and/or electrical conductivities. Military vehicles normally have smoother surfaces and a lower electrical conductivity. Consequently, as the polarizer is rotating, the background surrounding the military vehicle gives a steady signal which is not highlighted to the eye. The fluctuating targets stand out, giving away their location. Neither camouflage nor moderate foliage stops the systems from highlighting military targets because adequate flashing still can be observed. This system is also applicable to detecting high-tension electrical wires.

In one embodiment, the polarizer is mounted at each optical array of a set of binoculars. A motor and gear drive gear teeth mounted to the perimeter of the polarizer. The observer will see flashes of smooth man-made objects as the polarizer rotates while the background remains uniform. The flashes pinpoint military targets to an observer. This flashing can be also observed by a polarizer being rotated in the optical path of an infrared camera and a video camera.

Other embodiments will further distinguish if the object being detected has both horizontal and vertical surfaces and distinguish sky and water from man-made objects. A natural horizontal surface such as a lake will reflect light which will polarize. Consequently, flashes would appear as the polarizer rotates. Similarly, on clear days, the light from certain parts of the sky will polarize, also providing flashes proportionate to the speed of rotation. Water surfaces reflect the sky condition. Man-made targets will have both generally horizontal and vertical surfaces, unlike the sky or a body of water. Consequently, a rotating polarizer will flash each time the lines are horizontal and each time the lights are vertical. On the other hand, if the lens is pointed toward a body of water, the flash would occur only after the lens is moved out of its horizontal orientation. Consequently, only one-half of the flashes would be observed, and the man-made target can be distinguished from this background.

In one embodiment, background which polarizes is eliminated and discriminated from three-dimensional man-made objects by utilizing a video camera. The polarizer mounts in the optical train of the camera and rotates in the same manner as with the binoculars, although preferably faster. A frequency filter will filter out all background that fails to fluctuate in intensity at least at a rate equal to the speed of rotation. Moving natural objects which fluctuate in light intensity, such as fluttering leaves are filtered out because of the lower frequency. Completely stationary background is also eliminated. An electronic circuit will time the speed and rotational position and determine if flashing is occurring both when the polarizer is oriented horizontally and when oriented vertically. A mixing circuit will add the signals only if both a horizontal and a vertical component for the object is detected. This indicates a three-dimensional man-made object has been observed.

In another embodiment, rather than a video camera, an infrared detector is utilized. This system can be utilized at night as well as day. Tests have demonstrated that a polarizer will polarize infrared radiation in the same manner a visible light.

In another embodiment, rather than rotating the lenses, two video cameras are employed. A vertically-oriented polarizer mounts stationarily in front of one video camera. A horizontally-oriented polarizer mounts stationarily in front of the other video camera. The video camera scanning electrodes are synchronized. Each point scanned by one video camera electrode gun is compared to the other video camera. If the same point appears brighter to one camera than in the other, then this indicates that light is being polarized differently through the other of the lenses.

For example, a brighter portion of an object seen through the vertically-oriented polarizer indicates that a horizontal reflecting surface has been located. Similarly, a brighter portion observed by the video camera which has the horizontally-oriented polarizer than the other indicates that a vertical surface reflecting light that has been polarized has been located. If both of these conditions occur, then it indicates that a three-dimensional man-made object has been located. Circuitry will display the object on a monitor.

The system sees no difference for natural items such as dirt, trees, mountains and most skies. The system eliminates these images from the screen and displays only the man-made targets. This background elimination is important for reconnaissance.

DETAILED DESCRIPTION OF INVENTION

Figure 1:
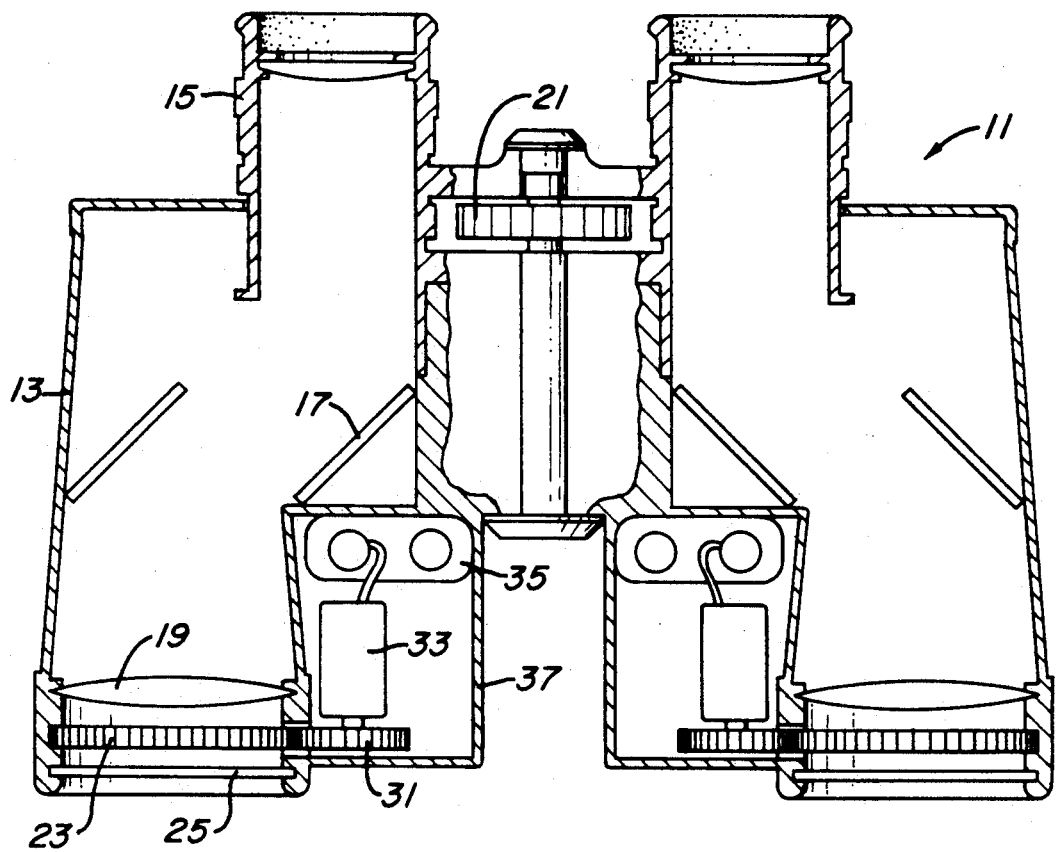
FIG. 1 shows a schematic sectional view of a pair of binoculars having polarizers constructed in accordance with this invention.

Referring to FIG. 1, binoculars 11 have a basic conventional design and are normally much more detailed than shown. Binoculars 11 will include a housing 13 Two eyepieces 15 mount telescopingly to housing 13. Mirrors 17 located within the housing 13 reflect light passing inward through a lens 19. A focal adjuster 21 will vary the distance between the eyepiece 15 and the lens 19 for focusing. Normally, the optical array will include other lenses as well.

Figure 2:
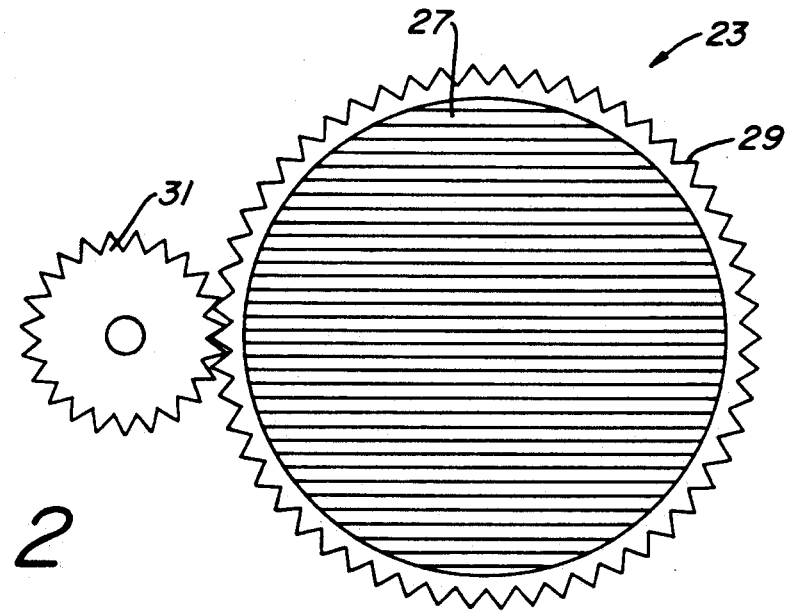
FIG. 2 is an enlarged, schematic, front view of one of the polarizers of FIG. 1.

In this invention, a polarizer 23 is mounted to each optical array in the image path. Preferably, polarizer 23 is mounted in front of the first lens 19 but may be protected by a glass cover 25 on the exterior, and may also be mounted within the optical train. Each polarizer 23 is a conventional commercially available polarizer. As shown in FIG. 2, each has a large number of lines 27 formed thereon, which may be scribed or otherwise etched on the surface. Also, the polarizer 23 may be formed by a chemical coating which aligns the molecules in parallel lines. Polarizer cubes are also commercially available. Lines 27 are extremely closely spaced and are parallel to each other. FIG. 2 exaggerates the distance between lines 27, as the distance would normally not be visible to the naked eye. The distance between lines 27 is less than the wavelength of light for which the polarizer is designed. Both polarizers 23 must be oriented the same at all times, and are synchronized with the same speed of rotation.

Polarizers such as polarizer 23 have been known in the past. It is known that they will remove the glare from light reflected from objects when the lines are oriented horizontally. This occurs as a result of light waves striking the reflecting object being unable to pass through the finely separated lines 27.

If polarizer 23 is rotated such that lines 27 are not substantially horizontal, then the glare will return as the light waves will be able to pass through the polarizer 23. The lines 27 will be invisible in either event to the observer. Rotating polarizer 23 will thus result in a reflecting object flashing in proportion to the speed of rotation. For visual determinations of the flash, revolutions of about 2 to 4 per second are desired. If the object being observed is of a type that is man-made, having a smooth appearance and having both vertical and horizontal surfaces, then flashes will occur both when the polarizer 23 has its lines 27 oriented horizontally and when oriented vertically. At 2 to 4 revolutions per second, approximately 7 flashes per second would be observed to the human eye. This is a flash rate that will naturally draw the eye/mind system's attention.

The rotation means for rotating polarizer 23 includes a set of gear teeth 29 formed on the circular perimeter of each polarizer 23. Gear teeth 29 may be formed integrally or may be formed on a ring that is secured or pressed fitted to the perimeter of polarizer 23. A drive gear 31 has teeth which will engage teeth 29. A DC electrical motor 33 will drive drive gear 31. A battery 35 supplies power for motor 33. A switch (not shown) enables the observer to selectively turn motor S3 on and off.

In the operation of the embodiment of FIGS. 1 and 2, the observer will place his eyes next to eyepiece 15 and scan a selected terrain. If the observer is not actuating the motors 33, then the polarizers 23 will perform no function in particular. If the user actuates the motors 33, the polarizers 23 will begin to rotate at the same speed and with lines 27 at the same angular positions. Light reflected from man-made objects will appear to flash as the polarizers 23 rotate. Most natural objects in the background will not flash, because the reflected light from natural surfaces usually does not produce a strong polarizing contrast. The flashing will pinpoint military targets to the viewer.

When the polarizer 23 has its lines 27 oriented horizontally, vertical surfaces of a man-made object may appear bright, and horizontal portions of the object dull, because the light reflected therefrom will be polarized by the lines by the polarizer 23. The light reflected from the vertical surfaces of the object will not be polarized by the polarizer 23 when the lines 27 are oriented horizontally. When the lines 27 pass the vertical position, the vertical surfaces of the man-made object will reflect light that is polarized by the lines 27. Consequently, vertical surfaces will appear less bright than when viewed previously. providing a flash. Similarly, the horizontal surfaces of the object will not produce polarized reflected light because the lines 27 are vertical. This causes the horizontal surfaces to flash brighter. Three-dimensional man-made objects thus may reflect up to four flashes for each rotation.

Figure 3:
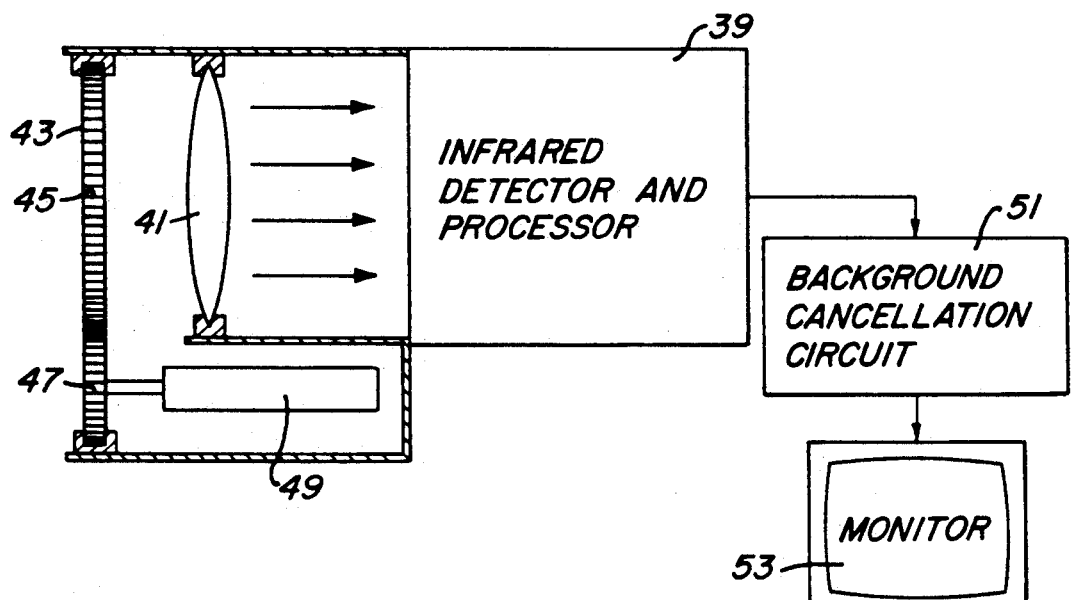
FIG. 3 is a schematic view illustrating an infrared detector having a polarizer mounted to it in accordance with this invention.

Referring to FIG. 3, in this embodiment, an infrared detector 39 is employed. Infrared detector 39 is of a conventional commercially available type. Lens 41 may be integrally contained with infrared detector 39. Preferably, it is a 3 to 5 micron or an 8 to 14 micron forward-looking infrared detection system.

A polarizer 43 is mounted into infrared detector 39 in front of lens 41 or in the optical train. Polarizer 43 is also a commercially available item. It will have polarization designed for 1 to 14 micron wavelength, different than polarizer 23 (FIG. 1). Polarizer 43 also has a drive means for rotating it about an axis of rotation concentric with the lens array. This includes gear teeth 45 located on the perimeter of polarizer 43. A drive gear 47 engages gear teeth 45. A motor 49 will rotate drive gear 47. Motor 49 will be connected to a power source.

Images detected by infrared detector 39 are polarized by polarizer 43. These images will appear different when polarizer 43 is in a polarizing position than otherwise. The differences can be visibly detected by an observer if the rotation speed is slow enough. Preferably, the speed of rotation is above 200 r.p.m., too high for flashes to be visibly observed without further processing. Rather, the signals from infrared detector 39 first pass through a background cancellation circuit 51, then to a display monitor 53 for observing by an observer. Background cancellation circuit 51 will be described in more detail subsequently. It serves to eliminate from monitor 53 all objects that do not flash proportional with the rotational speed of the polarizer 43. These objects include most natural objects, such as trees, foliage, earth and the like, due to the texture of these surfaces, and some man-made objects such as camouflage.

Background cancellation circuit 51 also performs an additional function which is not performed by the binoculars 11 of FIG. 1. This function is to distinguish between objects which may be flashing as the polarizer 43 rotates, but which have only a horizontal or a vertical component, not both. Most man-made objects sought to be detected often have both horizontal and vertical surfaces. The background cancellation circuit 51 will pass to monitor 53 only those images detected which emanate infrared radiation that polarizes both when polarizer 43 is oriented with its lines horizontal and when oriented with its lines vertical.

Figure 4:
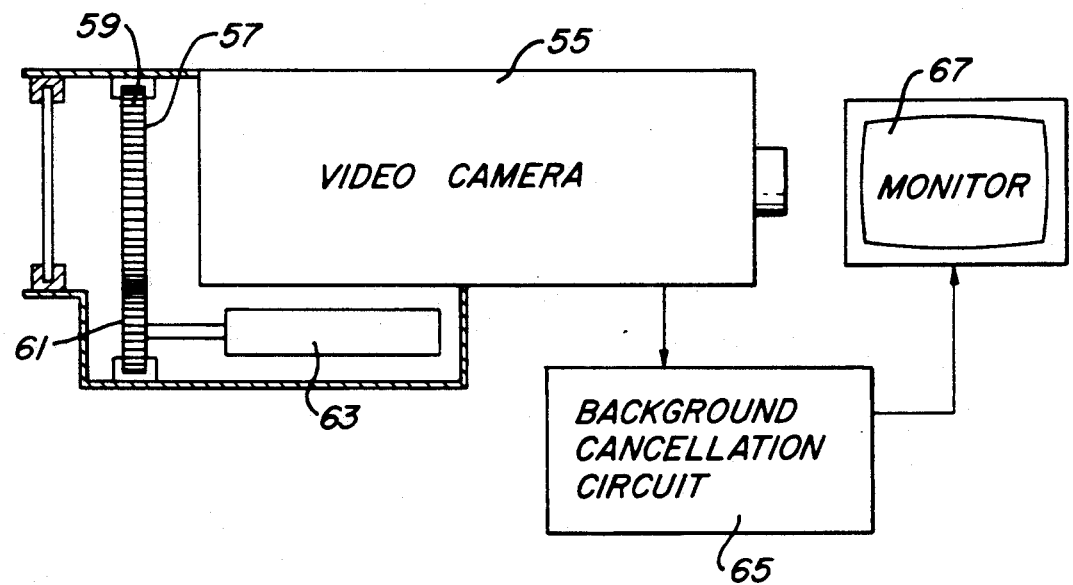
FIG. 4 is a schematic view of a video camera having a polarizer mounted to it in accordance with this invention.

Referring to FIG. 4, the third embodiment is shown. In this embodiment, rather than an infrared detector 39, a video camera 55 is employed. Video camera 55 is of a conventional type. Objects viewed by video camera 53 are converted into electrical signals which are displayed electronically. A polarizer 57 mounts to video camera 55 on an axis of rotation directly in front of or within its optical lens system. Polarizer 57 has a plurality of gear teeth 59 on its perimeter. A drive gear 61 will rotate polarizer 57 about its axis of rotation. A motor 63 will supply power to rotate drive gear 61. Preferably, the speed of rotation is above 200 r.p.m.

Video camera 55 will produce flashing or pulsing images reflected from man-made objects having smooth non-light conducting surfaces. This flashing can be visually observed by an observer if the rotational speed was slower. Preferably, the signals, however, are initially processed by a background cancellation circuit 65 and are than fed to a monitor 67. Background cancellation circuit 65 will eliminate all background which does not produce flashing as a result of the rotation of polarizer 57. Secondly, background cancellation circuit 65 will selectively delete objects which flash only when polarizer 57 is in a horizontal orientation or in a vertical orientation. Consequently cancellation circuit 65 will not pass signals representing sky or lakes to monitor 67. Only an object having both generally horizontal and vertical surfaces that reflect light which polarizes will be displayed by monitor 67.

Figure 5:
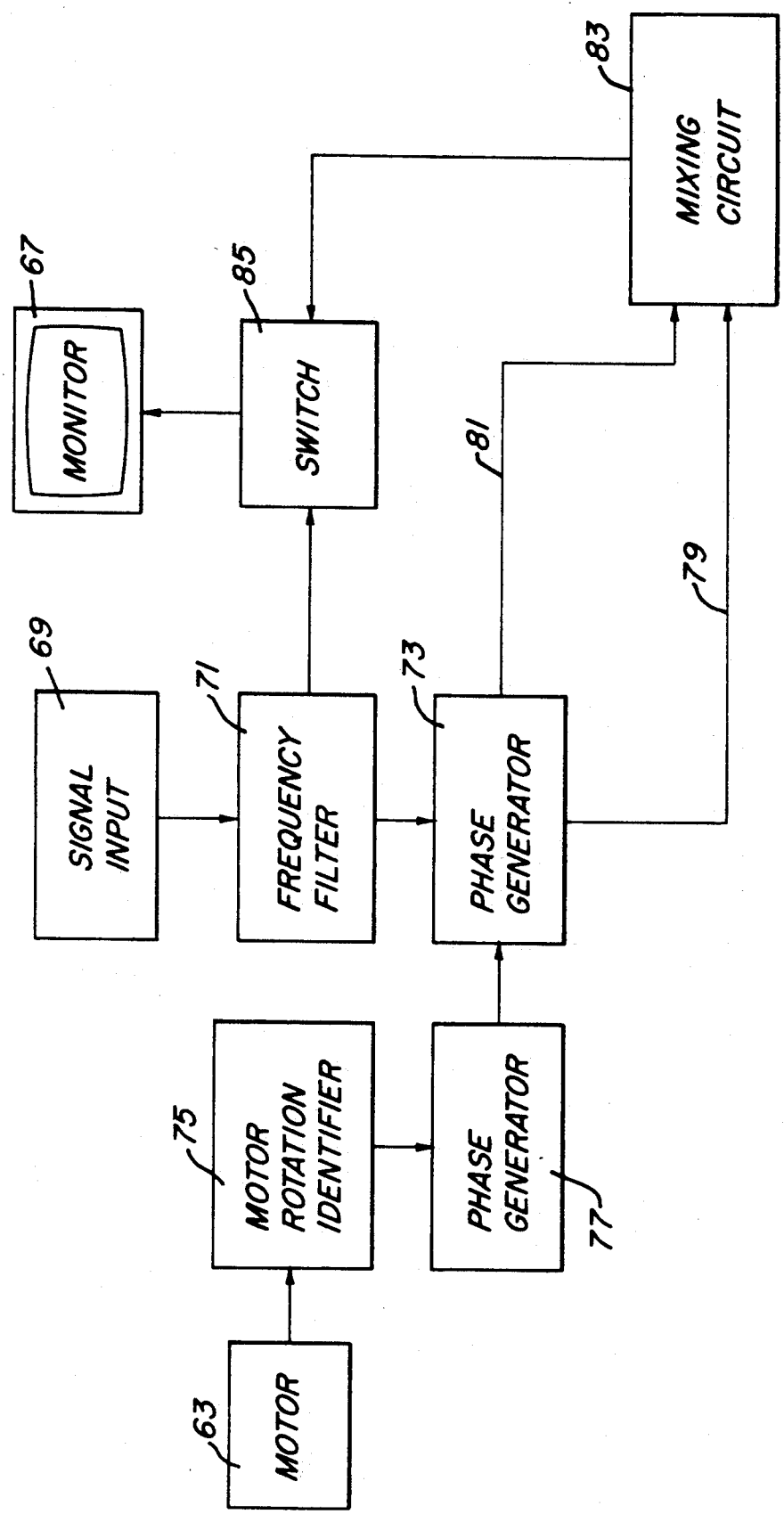
FIG. 5 is a more detailed block diagram of the background cancellation circuit utilized with the infrared detector of FIG. 3 and with the video camera of FIG. 4.

FIG. 5 represents more details of the background cancellation circuit 65. FIG. 5 also represents the background cancellation circuit 51 for the infrared detector 39 in FIG. 3. The circuit 65 will include a signal input 69 which receives electrical signals from video camera 55 based on scanning by camera 55. A frequency filter 71 will filter all frequencies below those that flash at or above the rotation of motor 63. Filter 71 is an electronic filter, passing electrical signals that have amplitude changes representing changes in light intensity seen of a particular object or portion of an object as a result of the rotation of polarizer 57. The amplitude changes must be at a frequency above the setting of filter 71 in order to pass. Consequently light contrast due to fluctuating leaves would not pass as the frequency would be below the minimum.

Signals that pass through frequency filter 71 will pass to a phase comparator 73. At the same time, a motor rotation identifier 75 will be monitoring accurately the speed of rotation of motor 63. Motor rotation identifier 75 leads to a phase generator 77. Phase generator 77 and motor rotation identifier 75 will continuously and precisely determine not only the speed of rotation, but also the instantaneous orientation of the lines contained on the polarizer 57. Phase generator 77 will generate a signal that indicates when the lines of polarizer 57 are in a horizontal position. A different signal will be generated indicating when phase generator 77 has its lines oriented vertically. These alternating signals are 90 degrees out of phase with each other and are applied to the phase comparator 73.

The phase comparator 73 will compare the alternating signal from the phase generator 77 to determine if a lesser intensity signal, or polarization, occurred simultaneously when the polarizer 57 was horizontal. Similarly, phase comparator 73 will determine if a lesser intensity signal or polarization occurred when the polarizer 57 was vertical. If polarization occurred when polarizer 57 was vertical, the signal passes from phase comparator 73, as indicated by output signal 81. If polarization occurred when polarizer 57 was horizontal, a signal will pass from phase comparator 73, as indicated by output signal 79.

The vertical component signals 81 and the horizontal component signals 79 are applied to a mixing circuit 83. The mixing circuit 83 inverts one of the signals 79, 81 and adds the two. If a vertical component signal 81 immediately followed a horizontal component signal 79, then mixing circuit 83 will forward the combined signal through a switch 85 to monitor 67. Monitor 67 will visually display an object which has provided the vertical and horizontal component signals 81, 79. On the other hand, if a horizontal component 79 does not immediately follow a vertical component 81 in time sequence corresponding to the rotation of motor 63, then mixing circuit 83 will not provide a signal to monitor 67. The added signals would not meet a threshold in mixing circuit 83. This condition indicates that the object was flashing only when polarizer 57 was either vertical or horizontal not in both positions. This indicates that the object is not a man-made object having vertical and horizontal surfaces. Therefore, it is excluded from monitor 67.

Switch 85 is manually accessible. It allows the operator to selectively pass the signals from frequency filter 71 directly to monitor 67. The operator in this manner could visually determine if an object is of interest, rather than utilizing the circuitry which excludes objects not having horizontal and vertical components.

Figure 6:
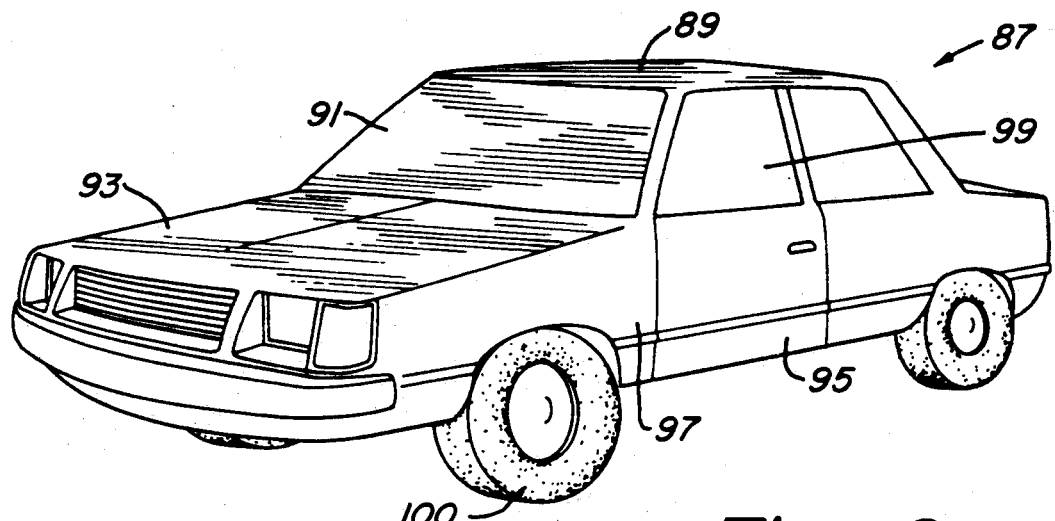
FIG. 6 is a perspective view of a vehicle illustrating light being polarized by a horizontally-oriented polarizer.
Figure 7:
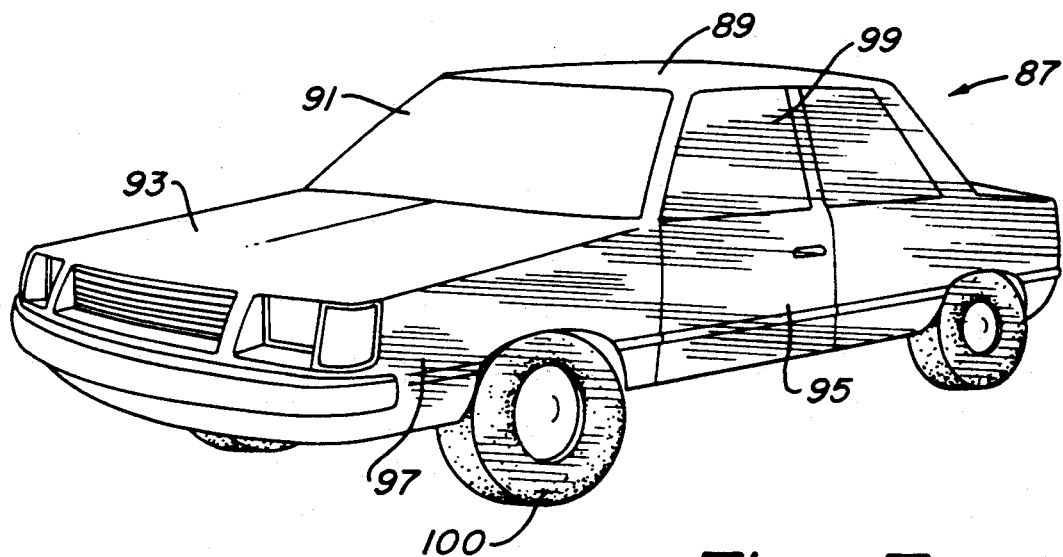
FIG. 7 illustrates the vehicle of FIG. 6 with the light being polarized when the polarizer is in a vertical position.

FIGS. 6 and 7 illustrate the types of horizontal and vertical components that may be observed and detected with the circuitry of FIG. 5. Vehicle 87 has a roof 89 that will be horizontally oriented if on flat terrain.

Windshield 91 inclines, thus possibly providing both vertical and horizontal reflections, but normally will reflect more in a horizontal mode as does roof 89. Hood 93 is typically in approximately the same plane as roof 89. Doors 95, fenders 97, side windows 99 and tires 100 will normally be nearly vertical. The darkened lines in FIGS. 6 and 7 show the differences in polarizing contrast that occurs due to rotation of polarizer 57. These differences also occur and may be seen visibly with the polarizer 23 of FIG. 1.

In FIG. 6, the vertical surfaces from door 95, fender 97, side windows 99 and tires 100 are reflecting light which is not being polarized. This indicates that the polarizer 57 is oriented other than with its lines vertical. Conversely, the flat horizontal surfaces of roof 89, windshield 91 and hood 93 reflect light which is being polarized. These reflections are occurring in the horizontal plane, confirming that polarizer 57 is oriented with its lines in a horizontal position. In FIG. 7, the reverse occurs. Roof 89, windshield 91 and hood 93 reflect light that is not polarized, while door 95, fender 97, side windows 99 and tires 100 reflect light that is polarized. This indicates that the polarizer 57 has rotated to a vertical position in which its lines are oriented vertically, 90 degrees from the position observed in FIG. 6.

In the operation of the embodiment of FIGS. 4 and 5, motor 63 rotates polarizer 57. Assuming that video camera 55 is pointed at vehicle 87 of FIGS. 6 and 7, flashes will occur. The video camera 55 will produce a signal 69 (FIG. 5) which represents not only the flashes from vehicle 87, but also all of the background being observed, such as the surrounding trees, hills and other terrain. Frequency filter 11 will pass only signals which are cycling in intensity at a minimum frequency indicating that the flashing is due to rotation of polarizer 57. As no flashing will occur, or very little, due to the natural terrain, the signals representing the terrain will be blocked. The signals representing most of the vehicle 87 will pass through frequency filter 71. If switch 85 is in one position, flashing portions of the vehicle 87 will then be displayed on monitor 67.

At the same time, phase comparator 73 will compare the flashing being observed to an alternating signal produced by phase generator 77. Phase comparator 73 will determine if polarizing occurs when the polarizer 57 is oriented with its lines vertical. If so, vertical component 81 then passes to mixing circuit 83. This occurs as illustrated in FIG. 7, with the door 95, fenders 97, side windows 99 and tires 100 producing reflected light that is polarized due to the vertical orientation of polarizer 57. The reflection from roof 89 windshield 91 and hood 9S is not polarized. Phase comparator 73 also determines if polarizing occurs when phase generator 77 indicates that the polarizer 57 is oriented horizontally. If so, horizontal component 79 passes to mixing circuit 83. This is the instance that occurs in FIG. 6. In that figure, light reflected from roof 89, windshield 91 and hood 93 is polarized due to the horizontal orientation of polarizer 57. Now, the reflection from door 95, fenders 97, side windows 99 and tires 100 is not polarized.

Mixing circuit 83 will pass the signal on to monitor 67 if switch 85 is in the proper position and if it receives both components 79, 81 in alternating sequence. If the object was a body of water, then no signal would pass from mixing circuit 83, because it would not produce reflected light that would cause a flash to occur both when the polarizer 57 is oriented horizontally and oriented vertically.

Figure 8:
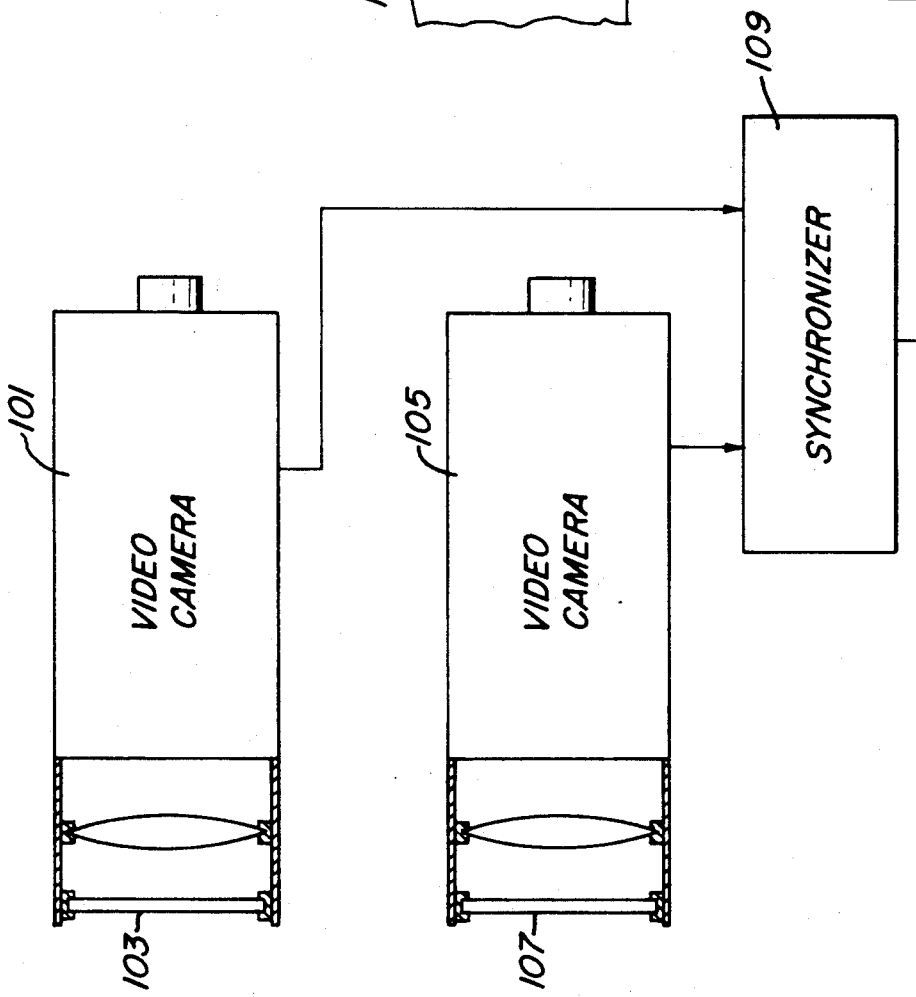
FIG. 8 is a schematic block diagram illustrating two video cameras having polarizers and associated circuitry in accordance with this invention.

FIG. 8 illustrates an embodiment that will perform the same function, but using a polarizer that does not require rotation. In FIG. 8, a video camera 101 has a horizontal polarizer 103 mounted stationarily to it. Polarizer 103 has its lines oriented horizontally and will not rotate relative to video camera 101. Consequently, any signals output from video camera 101 would represent only objects which produce a reflected light that polarizes in a horizontal plane. The object would thus be oriented with a generally horizontal surface.

Video camera 105 is of the same type as video camera 101. It has a vertical polarizer 107. Vertical polarizer 107 is identical to horizontal polarizer 103, except that it has its lines oriented vertically, 90 degrees from the lines of horizontal polarizer 103. Consequently, any signal produced by video camera 105 will polarize only light reflected from a generally vertical surface.

A synchronizer 109 synchronizes the video cameras 101, 105. That is, the electron gun contained within each video camera 101, 105 must be scanning the same object precisely at the same time. Each pixel or output of each video camera 101, 105 must be simultaneous in time. Note that the signals output from synchronizer 109 will not be pulsing, because polarizers 103, 107 are not rotating. However, if a man-made object, such as vehicle 87 of FIGS. 6 and 7 is being observed, the signals will be different. The pixel representing a portion of windshield 91 from one camera 101, 105 would be of greater intensity than from the other camera 101, 105, because of the orientation of polarizers 103, 107. An observer would see vehicle 87 as shown in FIG. 6 with video camera 101, while the same observer would see vehicle 87 as shown in FIG. 7 with video camera 105. Similarly, a pixel representing an image of a point on door 95 as seen through camera 101 would be brighter than the same pixel representing the identical point on door 95 as seen by camera 105.

The differences in intensities of these pixels of the same points pass to a comparator 111. Comparator 111 compares the differences in intensities between each pixel point. If a sufficient magnitude appears, comparator 111 will pass the signal to monitor 113. The observer watching monitor 113 will see a substantial portion of the vehicle 87, but no background.

Figure 9:
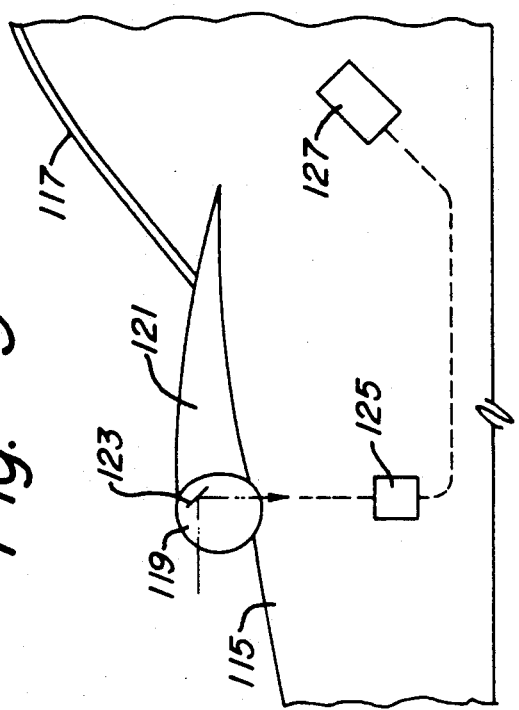
FIG. 9 is a schematic side view of a portion of an airplane having a detection system constructed in accordance with this invention.

FIG. 9 illustrates a portion of a fuselage 115 of an airplane. Fuselage 115 has a canopy 117. A transplant ball 119 rotatably mounts to fuselage 115, in front of and to one side of canopy 117. Ball 119 can be rotated for alignment and contains focusing lens system which focuses light onto a mirror 123. A mirror 123 reflects light down to a detection system 125 inside fuselage 115. Detection system 125 provides a signal over wires to a monitor 127 located in the cockpit. In the prior art, a similar arrangement is used for conventional infrared surveillance. Detection system 125 in this application would be either infrared detector 39 (FIG. 3), video camera 55 (FIG. 4), or video cameras 101, 105 (FIG. 8). An optical system, similar to binoculars 11 could also be employed in some cases.

The invention has significant advantages. It allows military target detection through camouflage and light foliage. The system can be mounted into binoculars to heighten enemy detection identification. The polarizing lenses and associated rotating drive system can be added without significant expense to existing binoculars. The binoculars can be used in an ordinary manner if desired. The system can be employed with infrared detectors to determine target detection and identification. Warm animals having fur do not provide a polarized difference because of their texturing. Vehicles and other man-made objects with smooth surfaces do provide differences when polarized. This avoids false targets due to animals for the infrared region. The system can be employed in helicopters to prevent pilots from colliding with power cables.

Additionally, the system could feasibly be used to prospect for special ores. The system will detect veins of non-conducting platelet type ores such as bauxite. Because of gold's pure natural state, it will have a smooth appearance and the system will locate these veins as well.

The system could also be employed in a manufacturing operation. It could separate electrical-conducting components in a manufacturing-type setting from those that do not conduct electricity. Similarly, the system could separate materials made from conducting material and those made from materials that are not electrical conductors.

While the invention has been shown in only a few of its forms, it should be apparent to those skilled in the art that it is not so limited but is susceptible to various changes without departing from the scope of the invention. For example, the invention could be employed in night vision goggles.

I claim:

1. An apparatus for searching for selected objects, comprising in combination:
   a lens array defining an image path for viewing objects at which the apparatus is pointed; and
   polarizer means mounted to the apparatus in the image path for horizontally and vertically polarizing light received from objects and transmitted through the image path to capture a first image of the objects during horizontal polarization and a second image of the objects during vertical polarization, and for alternately detecting the first and second images in rapid sequence to determine if any of the objects of the first and second images appear to alternately flash as a result of a difference existing between polarized light from the object when horizontally polarized and when vertically polarized, indicating that a selected object exists.

2. The apparatus according to claim 1 wherein the polarizer means comprises:
   a polarizer mounted in the image path, the polarizer being capable of polarizing light horizontally when oriented in a horizontal position, and polarizing light vertically when oriented in a vertical position; and
   means for moving the polarizer between the horizontal and vertical positions.

3. The apparatus according to claim 1 wherein the polarizer means comprises:
   a polarizer mounted in the image path on an axis of rotation; and
   rotational means for rotating the polarizer about the axis of rotation.

4. The apparatus according to claim 1 wherein the polarizer means comprises:
   a polarizer mounted in the image path on an axis of rotation;
   a motor; and
   drive means located between the motor and polarizer for rotating the polarizer about the axis of rotation.

5. An apparatus for searching for selected objects, comprising in combination:
   a lens array defining an image path for viewing objects at which the apparatus is pointed;
   polarizer means mounted to the apparatus in the image path for horizontally and vertically polarizing light received from objects and transmitted through the image path, and for determining if a difference exists between polarized light from the object when horizontally polarized and when vertically polarized, indicating that a selected object exists; and wherein the polarizer means comprises:
   a polarizer mounted in the image path on an axis of rotation, the polarizer having a perimeter containing a set of gear teeth;
   a motor; and
   a drive gear mounted to the motor for rotation therewith and in engagement with the gear teeth for rotating the polarizer about the axis of rotation.

6. The apparatus according to claim 1 wherein the lens array is an optical array for receiving and passing visible light reflected from the object.

7. An apparatus for searching for selected objects, comprising in combination:
   a lens array defining an image path for viewing objects at which the apparatus is pointed;
   polarizer means mounted to the apparatus in the image path for horizontally and vertically polarizing light received from objects and transmitted through the image path, and for determining if a difference exists between polarized light from the object when horizontally polarized and when vertically polarized, indicating that a selected object exists;
   means for determining if a first condition exists wherein a portion of the object being observed reflects more intense light when the polarizer means is polarizing light horizontally than when polarizing light vertically;
   means for determining if a second condition exists in which a portion of the object being observed reflects more intense light when the polarizer means polarizes light vertically than when polarizing light horizontally; and
   means for providing an indication to a viewer if both of said conditions exist, indicating an object which has generally horizontal and vertical surfaces, both of which reflect light which will polarize.

8. The apparatus according to claim 1 wherein the lens array is a video camera means which electronically displays the object being observed.

9. The apparatus according to claim 1 wherein the lens array is an infrared detector means for detecting infrared radiation from the object being observed and for displaying the object in a form proportional to different intensities of infrared radiation being detected.

10. The apparatus according to claim 1, further comprising means for mounting the apparatus to a fuselage of an airplane.

11. An apparatus for searching for selected objects, comprising in combination:
    a lens array defining an image path for viewing objects at which the apparatus is pointed;
    a polarizer mounted in the image path on an axis of rotation;
    rotational means for rotating the polarizer about the axis of rotation to cause objects reflecting light that is polarized to alternately contrast in intensity in proportion to the speed of rotation; and means for detecting any of the alternately contrasting intensities occurring as the rotational means rotates the polarizer, thereby indicating the presence of objects which reflect light that will polarize, and for displaying images of said objects without subtracting and adding the alternately contrasting intensities.

12. The apparatus according to claim 11 wherein the rotational means comprises:

a motor; and drive means between the motor and the polarizer for rotating the polarizer about the axis of rotation; and wherein the means for detecting includes means for displaying to an eye of a human observer any of the alternating contrasts in intensity that occurs as the polarizer is rotated, the alternating contrasts appearing as flashing to the eye of the human observer.

13. An apparatus for searching for selected objects, comprising in combination:

a lens array defining an image path for viewing objects at which the apparatus is pointed;

a polarizer mounted in the image path on an axis of rotation;

rotational means for rotating the polarizer about the axis of rotation to cause objects reflecting light that is polarized to alternately contrast in intensity in proportion to the speed of rotation; and wherein the rotational means comprises:

a generally circular perimeter on the polarizer;

a set of gear teeth on the perimeter of the polarizer;

a motor; and a drive gear mounted to the motor for rotation therewith and in engagement with the gear teeth of the polarizer for rotating the polarizer.

14. The apparatus according to claim 11 wherein the lens array is in an optical array for receiving and passing visible light reflected from the object being viewed.

15. The apparatus according to claim 11 wherein the rotational means rotates the polarizer through horizontal and vertical positions, and wherein the apparatus further comprises:

means for determining if a first condition exists wherein a portion of the object being observed reflects more intense light when the polarizer is in the horizontal position than when in the vertical position;

means for determining if a second condition exists in which a portion of the object being observed reflects more intense light when the polarizer is in the vertical position than when in the horizontal position; and means for providing an indication to a viewer if both of said conditions exist, indicating an object which has generally horizontal and vertical surfaces, each of which reflects light which will polarize.

16. The apparatus according to claim 11 wherein the lens array is a video camera means which processes visible light and electronically displays the object being viewed.

17. The apparatus according to claim 11 wherein the lens array is an infrared detector means for detecting infrared radiation from objects and for producing a display corresponding to different intensities of the infrared radiation being detected as the polarizer is rotated.

18. The apparatus according to claim 11, further comprising means for mounting the apparatus to a fuselage of an airplane.

19. A pair of binoculars for searching for targets, comprising in combination:

a pair of lens arrays, each including an eyepiece, defining an image path for viewing objects at which the lens arrays are pointed;

a pair of polarizers, each mounted to the binoculars in one of the image paths for rotation about an axis of rotation; and rotational means for rotating each of the polarizers relative to the lens arrays, causing reflected light received in the image path from certain objects to flash at frequencies proportional to the speed of rotation; and eyepiece means for each lens array for allowing a human observer to see any flashes that may be occurring as the polarizers rotate, the speed of rotation being selected to be such that the flashes are discernable to a human eye.

20. The apparatus according to claim 19 wherein the rotational means comprises:

a motor; and drive means mounted between the motor and the polarizer for rotating the polarizer in response to rotation of the motor.

21. The apparatus according to claim 19, wherein the rotational means comprises:

a circular perimeter on the polarizer;

a set of gear teeth located on the perimeter of the polarizer;

a motor; and a drive gear mounted to the motor for rotation therewith in engagement with the gear teeth of the polarizer.

22. An apparatus for searching for selected objects, comprising in combination:

infrared detector means having an image path for detecting infrared light emanating from objects at which the apparatus is pointed;

polarizer means mounted to the apparatus in the image path for horizontally and vertically polarizing light received from objects and transmitted through the image path into a first image occurring during horizontal polarization and a second image occurring during vertical polarization, and for rapidly alternating the first and second images to create flashing of objects that emanate infrared light which differs in intensity when polarized; and means for detecting said flashing and displaying said objects to a human observer without adding and without subtracting the first and second images.

23. The apparatus according to claim 22 wherein the polarizer means comprises:

a polarizer mounted in the image path, the polarizer being capable of polarizing light in a horizontal plane when oriented in a horizontal position, and polarizing light in a vertical plane when oriented in a vertical position, 90 degrees rotationally from the horizontal position; and means for moving the polarizer between the horizontal and vertical positions.

24. The apparatus according to claim 22 wherein the polarizer means comprises:

a polarizer mounted in the image path on an axis of rotation; and rotational means for rotating the polarizer about the axis of rotation.

25. The apparatus according to claim 22, wherein the polarizer means comprises:
a polarizer mounted in the image path on an axis of rotation;
a motor; and
drive means located between the motor and polarizer for rotating the polarizer about the axis of rotation.

26. An apparatus for searching for selected objects, comprising in combination:
infrared detector means having an image path for detecting infrared light emanating from objects in which the apparatus is pointed;
polarizer means mounted to the apparatus in the image path for horizontally and vertically polarizing light received from objects and transmitted through the image path, and for determining if a difference exists between the horizontal and vertical polarized light, indicating that a selected object exists; and wherein the polarizer means comprises:
a polarizer mounted in the image path on an axis of rotation, the polarizer having a perimeter containing a set of gear teeth;
a motor; and
a drive gear mounted to the motor for rotation therewith and in engagement with the gear teeth for rotating the polarizer about the axis of rotation.

27. The apparatus according to claim 22, further comprising means for mounting the apparatus to a fuselage of an airplane.

28. An apparatus for locating selected objects, comprising:
infrared detector means having an image path for detecting infrared light emanating from objects at which the apparatus is pointed;
a polarizer mounted in the image path on an axis of rotation;
rotational means for rotating the polarizer about the axis of rotation, creating a first image of objects that emanate polarized infrared light when the polarizer is in a first position and a second image of objects that emanate polarized infrared light when the polarizer is in a second position, thereby causing any light polarized to flash alternately as the polarizer rotates; and
means for detecting said flashes as the polarizer rotates, and for displaying said objects to a human observer without adding and without subtracting the first and second images.

29. The apparatus according to claim 28 wherein the rotational means comprises:
a motor; and
drive means between the motor and polarizer for rotating the polarizer.

30. An apparatus for locating selected objects, comprising:
infrared detector means having an image path for detecting infrared light emanating from objects at which the apparatus is pointed;
a polarizer mounted in the image path on an axis of rotation;
rotational means for rotating the polarizer about the axis of rotation, thereby causing any light polarized to flash alternately as the polarizer rotates; and wherein the rotational means comprises:
a set of gear teeth on a perimeter of the polarizer;
a motor; and
a drive gear mounted to the motor for rotation therewith and in engagement with the gear teeth of the polarizer for rotating the polarizer.

31. The apparatus according to claim 28, further comprising means for mounting the apparatus to a fuselage of an airplane.

32. An apparatus for locating selected objects, comprising:
infrared detector means having an image path for detecting infrared light emanating from objects at which the apparatus is pointed;
a polarizer mounted in the image path on an axis of rotation;
rotational means for rotating the polarizer about the axis of rotation, thereby causing any light polarized to flash alternately as the polarizer rotates; and wherein the polarizer has a plurality of spaced apart parallel lines and wherein the apparatus further comprises a discriminating means, which comprises:
means for determining the speed of rotation of the polarizer;
filter means for filtering out electrical signals representing background objects viewed which emanate light that does not differ when rotating the polarizer;
phase comparator means receiving a signal from the filter means for determining if the polarizer polarized light emanating form the object when the lines are in the horizontal position and when in the vertical position, and for producing a horizontal component signal and a vertical component signal corresponding thereto if polarization did occur during both positions; and
comparator means receiving each of the component signals from the phase comparator means for determining if a horizontal component signal is being received that alternates in time with a vertical component signal being received, and if so, passing the horizontal and vertical component signals to a display for viewing.

33. An apparatus for searching for selected objects, comprising in combination:
a video camera means having an image path for receiving reflected light from objects at which the video camera means is pointed;
polarizer means mounted to the apparatus in the image path for horizontally and vertically polarizing light received from objects and transmitted through the image path, creating a first image of objects which reflect horizontally polarized light and a second image of objects which reflect vertically polarized light, and for rapidly alternating the first and second images of light received from an object when horizontally polarized than when vertically polarized, creating flashing; and
means for detecting the flashing without adding and without subtracting the first and second images, indicating that a selected object exists.

34. The apparatus according to claim 33 wherein the polarizer means comprises:
a polarizer mounted in the image path, the polarizer being capable of polarizing light in a horizontal plane when oriented in a horizontal position, and polarizing light in a vertical plane when oriented in a vertical position, 90 degrees rotationally from the horizontal position; and means for moving the polarizer between the horizontal and vertical positions; and wherein the means for detecting comprises:

means for displaying said alternating first and second images to an eye of a human observer at a rate such that any of said flashing is discernable to the human observer.

35. The apparatus according to claim 33 wherein the polarizer means comprises:

a polarizer mounted in the image path on an axis of rotation; and rotational means for rotating the polarizer about the axis of rotation; and wherein the means for detecting comprises:

means for displaying said alternating first and second images to an eye of a human observer at a rate such that any of said flashing is discernable to the human observer.

36. The apparatus according to claim 33 wherein the polarizer means comprises:

a polarizer mounted in the image path on an axis of rotation;

a motor; and drive means located between the motor and polarizer for rotating the polarizer about the axis of rotation; and wherein the means for detecting comprises:

means for displaying said alternating first and second images to an eye of a human observer at a rate such that any of said flashing is discernable to the human observer.

37. An apparatus for searching for selected objects, comprising in combination:

a video camera means having an image path for receiving reflected light from objects at which the video camera means is pointed, and for electronically displaying the image;

polarizer means mounted to the apparatus in the image path for horizontally and vertically polarizing light received from objects and transmitted through the image path, and for determining if a difference exists between light received from an object when horizontally polarized than when vertically polarized, indicating that a selected object exists; and wherein the polarizer means comprises:

a polarizer mounted in the image path on an axis of rotation, the polarizer having a perimeter containing a set of gear teeth;

a motor; and a drive gear mounted to the motor for rotation therewith and in engagement with the gear teeth for rotating the polarizer about the axis of rotation.

38. The apparatus according to claim 33, further comprising means for mounting the apparatus to a fuselage of an airplane.

39. An apparatus for detecting selected objects, comprising in combination:

a video camera means having an image path for receiving reflected light from objects at which the video camera means is pointed;

a polarizer mounted in the image path for rotation about an axis of rotation;

rotational means for rotating the polarizer about the axis of rotation to produce alternating contrasts in intensity of the light being polarized; and means for electronically displaying the alternating contrasts in intensity to a human observer as the polarizer is rotated, creating a flashing effect, the rate at which the polarizer is rotated being selected so that the flashing effect is discernable to the human observer.

40. The apparatus according to claim 39 wherein the rotational means comprises:

a motor; and drive means between the motor and the polarizer for rotating the polarizer.

41. An apparatus for detecting selected objects, comprising in combination:

a video camera means having an image path for receiving reflected light from objects at which the video camera means is pointed and for electronically displaying the image;

a polarizer mounted in the image path for rotation about an axis of rotation;

rotational means for rotating the polarizer about the axis of rotation to produce alternating contrasts in intensity of the light being polarized; and wherein the polarizer has a circular perimeter, and wherein the rotational means comprises:

a set of gear teeth located on the perimeter of the polarizer;

a motor; and a drive gear mounted to the motor for rotation therewith in engagement with the gear teeth for rotating the polarizer.

42. An apparatus for detecting selected objects, comprising in combination:

a video camera means having an image path for receiving reflected light from objects at which the video camera means is pointed and for electronically displaying the image;

a polarizer mounted in the image path for rotation about an axis of rotation;

rotational means for rotating the polarizer about the axis of rotation to produce alternating contrasts in intensity of the light being polarized; and wherein the polarizer has a plurality of spaced apart parallel lines and wherein the apparatus further comprises a discriminating means, which comprises:

means for determining the speed of rotation of the polarizer;

filter means for filtering out electrical signals representing background objects viewed which reflect light that does not differ when passing through the rotating polarizer;

phase comparator means receiving the signal from the filter means for determining if the polarizer polarized light reflected from the object when the lines are in a horizontal position and when in a vertical position, and for producing a horizontal component signal and a vertical component signal corresponding thereto if polarization did occur during both positions; and comparator means receiving each of the signals from the phase comparator means for determining if a horizontal component signal is being received that alternates in time with a vertical component signal being received, and if so, passing the horizontal and vertical component signals to a display for viewing.

43. The apparatus according to claim 39 further comprising means for mounting the apparatus to a fuselage of an airplane.

44. An apparatus for searching for selected objects, comprising in combination:

a pair of video cameras for scanning objects at which the video cameras are pointed, and for electronically displaying an image of the object;

a horizontal polarizer mounted stationarily to one of the video cameras for polarizing light reflected from an object which has a generally horizontal surface;

a vertical polarizer mounted stationarily to the other of the video cameras for polarizing light reflected from an object which has a generally vertical surface;

means for synchronizing the two video cameras so that each scans the same object simultaneously and at identical rates;

means for determining if a portion of an object appears brighter in the camera having the vertical polarizer than in the video camera having the horizontal polarizer, indicating that an object is being observed that reflects light that is capable of being polarized and which has a generally horizontal surface; and means for determining if a portion of an object appears brighter in the video camera having the horizontal polarizer than in the video camera having the vertical polarizer, indicating that an object is being observed which has a generally vertical surface that is capable of reflecting light that may be polarized; and means for displaying the object being viewed if the video cameras have detected an object which has both generally horizontal and generally vertical surfaces which will reflect light capable of being polarized.

45. The apparatus according to claim 44 further comprising means for mounting the apparatus to a fuselage of an airplane.

46. A Method for searching for selected objects, comprising:

providing a lens array which will define an image path;

mounting a polarizer in the image path;

pointing the lens array at objects;

passing light reflected from the objects through the polarizer and determining if any of the light will horizontally polarize, creating a first image and determining if any of the reflected light will vertically polarize, creating a second image;

rapidly alternating the first and second images so as to create flashing of certain objects due to the difference between horizontal and vertical polarizing; and displaying said certain objects to an observer without adding and without subtracting the first and second images, thereby indicating an object exists which has generally horizontal and vertical surfaces capable of polarizing light.

47. A Method for searching for selected objects, comprising:

providing a lens array which will define an image path;

mounting a polarizer in the image path;

pointing the lens array at objects;

passing light reflected from the objects through the polarizer and determining if any of the light will horizontally polarize and determining if any of the reflected light will vertically polarize;

determining the difference, if any, which exists when horizontally and vertically polarizing the reflected light, thereby indicating an object exists which has generally horizontal and vertical surfaces capable of polarizing light;

determining if a first condition exists wherein a portion of the object reflects brighter light when horizontally polarized than when vertically polarized;

determining if a second condition exists wherein a portion of the object reflects brighter light when vertically polarized than when horizontally polarized; and providing an indication to a viewer if both of said conditions exist, indicating an object which has surface that is generally horizontal, and another surface that is generally vertical, both of the surfaces being capable of reflecting light that may be polarized.

48. The method according to claim 46 wherein the steps of horizontally and vertically polarizing light ar performed rotating the polarizer about an axis of rotation; and wherein the step of alternating the first and second images is performed at a rate selected such that the flashing is discernable to a human eye.

49. The method according to claim 46 wherein the step of providing a lens array comprises providing a pair of binoculars, and viewing the object through the binoculars; and wherein the step of alternating the first and second images is performed at a rate selected such that the flashing is discernable to a human eye.

50. The method according to claim 46 wherein the step of providing a lens array comprises providing a video camera and electronically displaying the object with the video camera; and wherein the step of alternating the first and second images is performed at a rate selected such that the flashing is discernable to a human eye.

51. The method according to claim 46 wherein the step of providing a lens array comprises providing an infrared detector and electronically displaying the infrared light being detected.

52. A method for searching for selected objects, comprising:

providing a lens array having an image path;

providing a polarizer;

mounting the polarizer about an axis of rotation in alignment with the image path of the lens array;

rotating the polarizer about the axis of rotation; and monitoring the light passing through the polarizer and lens array to determine if flashing of certain objects in the image path exists as the polarizer rotates due to a difference in the intensity of light being received as the polarizer rotates.

53. A method for searching for selected objects, comprising:

providing a lens array having an image path;

providing a polarizer;

mounting the polarizer about an axis of rotation in alignment with the image path of the lens array;

rotating the polarizer about the axis of rotation;

monitoring the light passing through the polarizer and lens array to determine if a difference exists in the intensity of light being received as the polarizer rotates; and wherein the polarizer passes through horizontal and vertical positions as it rotates and wherein the method further comprises:

determining if a first condition exists wherein a portion of an object reflects brighter light when the polarizer is in a horizontal position than when in a vertical position;

determining if a second condition exists wherein a portion of an object reflects brighter light when the polarizer is in the vertical position than when in the horizontal position; and providing an indication to a viewer if both of said conditions exist, indicating an object which has a surface that is generally horizontal, and another surface that is generally vertical, both of the surfaces being capable of reflecting light that may be polarized.

54. The method according to claim 52 wherein the step of providing a lens array comprises providing a video camera and electronically displaying the object with a video camera; and wherein the step of rotating the polarizer is performed at a rotational speed selected such that said flashing is discernable to a human eye.

55. The method according to claim 52 wherein the step of providing a lens array comprises providing an infrared detector and electronically displaying the different intensities of the infrared light being detected.

56. A method for searching for selected objects comprising:

(a) providing a pair of video cameras and pointing the video cameras in the same direction;

(b) providing a pair of polarizers, each having a plurality of closely spaced parallel lines formed thereon;

(c) mounting one of the polarizers stationarily to one of the video cameras with its lines oriented horizontally;

(d) mounting the other of the polarizers to the other video camera with its lines oriented vertically;

(e) scanning an object with the video cameras and synchronizing the scanning with each of the video cameras so that each views the object and displays each portion of the object simultaneously;

(f) determining if a portion of an object being viewed appears brighter in the video camera containing the polarizer which is oriented with its lines vertically, than the video camera which has the polarizer with its lines oriented horizontally;

(g) determining if a portion of an object appears brighter in the video camera which has the polarizer with its lines oriented horizontally than the video camera which has the polarizer with its lines oriented vertically; and (h) determining if both of steps (f) and (g) exist, and if so displaying the object.

* * * * *